United States Patent [19]

Peck et al.

[11] Patent Number: 4,576,703
[45] Date of Patent: Mar. 18, 1986

[54] PREPARATORY ELECTROELUTION DEVICE

[75] Inventors: Lawrence J. Peck, Cambridge, Mass.; John H. Kreisher, Ridgefield; Alan L. Walker, New Haven, both of Conn.

[73] Assignee: International Biotechnologies, Inc., New Haven, Conn.

[21] Appl. No.: 668,571

[22] Filed: Nov. 5, 1984

[51] Int. Cl.[4] .......................................... G01N 27/28
[52] U.S. Cl. .............................. 204/299 R; 204/182.8
[58] Field of Search ............. 204/180 G, 299 R, 182.8

[56] References Cited

U.S. PATENT DOCUMENTS 3,969,218 7/1976 Scott ................................ 204/180 G
3,989,612 11/1976 Kragt et al. .................... 204/180 G
4,049,534 9/1977 Posner ............................ 204/299 R
4,234,400 11/1980 Kaplan et al. .................. 204/180 G

FOREIGN PATENT DOCUMENTS 552373 4/1977 U.S.S.R. .
616568 6/1978 U.S.S.R. .

Primary Examiner—John F. Niebling
Assistant Examiner—B. J. Boggs, Jr.
Attorney, Agent, or Firm—Bachman & La Pointe

[57] ABSTRACT

A novel receptacle for removing charged particles from a gel matrix or gel slice containing biological substances such as nucleic acids, proteins, carbohydrates and the like by electrophoresis procedures operable to recover and collect the particles in concentrated fashion with a minimum of undesirable fluid.

12 Claims, 4 Drawing Figures

PREPARATORY ELECTROELUTION DEVICE

BACKGROUND OF THE INVENTION

This invention relates to electrophoresis and in particular to a novel receptacle or apparatus useful to remove and collect charged particles of biological substances from gel slices in concentrated fashion with a minimum of undesirable fluid in the resultant concentrate.

A great number of electrophoresis devices exist taking advantage of the well known principle that charged particles suspended between poles of an electric field tend to migrate toward the pole whose charge is opposite to that of a given particle.

The so-called horizontal and vertical gel slab arrangements, examples of the use of the above principle, are utilized to separate charged particles.

In contrast, the present invention deals with elution and collection of particles of biological substances in concentrated form by means of electrophoresis hereinafter termed electroelution.

Classically elution of biological from electrophoresis gels is accomplished by extraction or electrophoresis using dialysis bags.

Extraction procedures are cumbersome, time consuming and ineffective.

Electroelution using dialysis bags is untidy, subject to bag leaks or bag tie leaks. Frequently, particles desired to be recovered adhere stubbornly to membranes after requiring current reversal to obtain release (frequently only partial release) leading to poor levels of recovery and unsatisfactory results.

In this background, the present invention provides a recovery apparatus that avoids the use of dialysis bags eliminating the potential for leaks and avoids the difficulty of gaining material release from membranes.

Therefore it is a principal object of the present invention to provide an improved electroelution device or apparatus.

Another object of the invention is the provision of a novel fluid system within the device.

A still further object of the invention is the provision of a novel valve structure useful in the fluid system.

Another object of the invention is the provision of an electroelution device operable to remove charged particles from gel slices where the particles are collected in concentrated fashion with a minimum of liquid present in the resultant concentrate.

A further object of the invention is the provision of a compact, accessible, convenient electroelution device that provides excellent operational visibility and is readily dismantled for cleaning.

SUMMARY OF THE INVENTION

An electroelution device embracing certain principles of the present invention may comprise at least two major fluid tight compartments separated by a bridge element, a first valve disposed in one compartment including a valve body and a valve stem within said valve body, a conduit connecting said valve body to the other compartment, through said bridge element, said valve stem having a central cavity defining a recovery reservoir, said valve stem being movable from a first position in which said valve is open so that said reservoir communicates through said conduit with an overflow outlet to a second position in which said valve is closed and said overflow outlet is cut off, said valve stem supporting at one end a gel specimen tray, a closure member for covering said tray and making a releasable keyed connection with said tray operable manually to move said stem to said first and second positions selectively.

BRIEF DESCRIPTION OF THE DRAWINGS

Other features and advantages of the invention will become apparent from an examination of the succeeding specification when read in conjunction with the appended drawings, in which.

DESCRIPTION OF PREFERRED EMBODIMENTS

Figure 1:
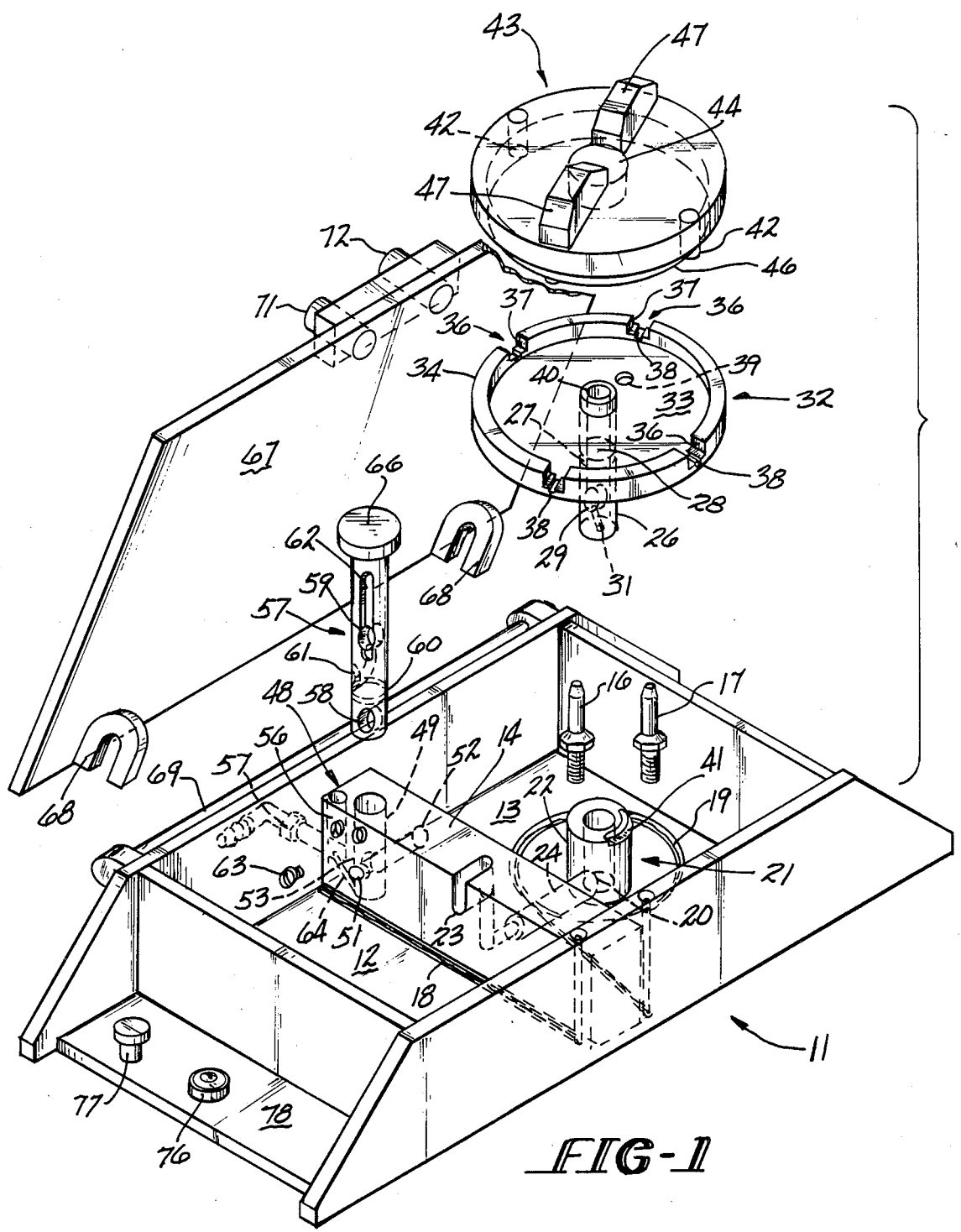
FIG. 1 is an exploded view, in perspective, of an electroelution device illustrating the principles of the invention.

Referring in detail to the drawings the electroelution receptable, indicated generally by the reference numeral 11, includes liquid tight buffer compartments 12 and 13 separated by a bridge 14. Electrical connectors 16 and 17 lead to electrodes 18 and 19 disposed in the base of compartments 12 and 13 respectively.

Compartment 13 contains a first valve 21 including valve body 22 communicating with an overflow outlet 23 via port 20 and conduit 24. Valve stem 26, encircled by a gasket or O-ring 27, is formed with a central reservoir 28 which in an open valve position communicates with said conduit 24 through its port 29 and valve body port 20.

Valve stem 26 is rotatable within valve body 22 from a first position in which said valve is open and said reservoir communicates with overflow outlet 23 via ports 20 and 29 and conduits 24 to a second or closed position in which said reservoir is sealed off from said overflow outlet. O-ring 27 in contact with the internal diameter of the valve body enhances the security of the closed valve position.

As shown in FIG. 1 the valve stem 26 is removable from the valve body 22 and to avoid an undesirable "fountain" effect upon inserting the stem a vent 31 angles from the base of the stem and intersects the stem port 29.

The valve stem 26 supports at its upper end a gel slice or gel specimen tray indicated generally by the reference numeral 32.

The tray has a recessed floor 33 encircled by a flange 34 interrupted by notches 36—36 which define key ways 37 and liquid flow paths or scuppers 38. The mouth 40 of the reservoir projects above the floor 33 and is generally co-planar with the top of flange 34.

A projection 39 extends from the underside of the floor 33 and engages in arcuate cut-out 41 in the valve stem cooperating when the stem is assembled in the valve body to provide a stop means for indicating the open and closed positions of the valve 21.

That is, when the projection 39 is at the right end of the cut-out 41 as viewed in FIG. 1 the valve is open or in the first position, when the projection 39 is rotated to the extreme left the valve is closed or in the second position.

The scuppers 38 provide a flow path for buffer fluid as will become more apparent hereinafter and the key ways 37 mate with keys 42—42 projecting from tray cover 43.

The cover 43 having a central bore 44, and an offset face 46 telescopes into the tray 32 making a loose fit around the mouth of the reservoir 28 and with the key ways. The keys 42 bottom in key ways 37 without blocking flow paths or scuppers 38 and the keys are so dimensioned vertically as to provide space for a gel specimen positioned upon the floor of the tray under the offset face 46 of the cover 43.

Buttons 47—47 are provided for convenient manual removal of the cover and to facilitate rotating the valve stem to open and close valve 21.

Note that electrode 19 in compartment 13 encircles valve 21 to equalize the effect of the electric field to enhance the flow of charged particles from the gel slice into the reservoir.

A second valve defining a spool valve indicated generally by the reference numeral 48 disposed in the bridge 14, includes a tubular body 49 having opposed first and second ports 51 and 52 and a third port 53 communicating with the atmosphere via conduit 54 and communicating with an overflow outlet 56 projecting upwardly from conduit 54.

A valve stem or spool 57 movable selectively into three positions includes a first opening 58, a second opening 59 and a third opening 61.

In the first position of the spool 57 opening 58 communicates with body ports 51 and 52 providing flow for buffer fluid through the bridge 14. In the second position of the spool the ports 51 and 52 are closed and a spool O-ring 60 enhances this closure.

In the third position of the spool 57 body ports 51 and 52 are opened and an outlet to atmosphere is provided for each buffer compartment 12 and 13 through second stem opening 59 and third stem opening 61 which intersects opening 59 internally of the stem 26.

Thus in the third position of the spool 57 buffer fluid in compartments 12 and 13 can drain to atmosphere through opposed valve body ports 51 and 52 mating opening 59 (second opening) of spool 57 thence to internal spool opening 61 (third opening) into and through conduit 54 to the exterior of the receptacle 11.

The first and third positions of the spool 57 are indicated by a control means defining a slot 62 in the spool and a cooperating set screw 63 in the valve body. Engagement of the bottom end of the slot with the set screw defines the first position of the valve while engagement of the upper end of the slot with the set screw defines the third position of the spool valve.

The second position is a medial position where communication between compartments 12 and 13 is cut off.

Here again a vent 64 is provided leading from the base of the interior of the valve body to the conduit 54 to eliminate siphon effect when the spool 57 is moved.

The spool 57 is provided with a head 66 which cooperates with a receptacle cover 67 in a manner which will be apparent when the operation of the receptacle is described.

Figure 2:
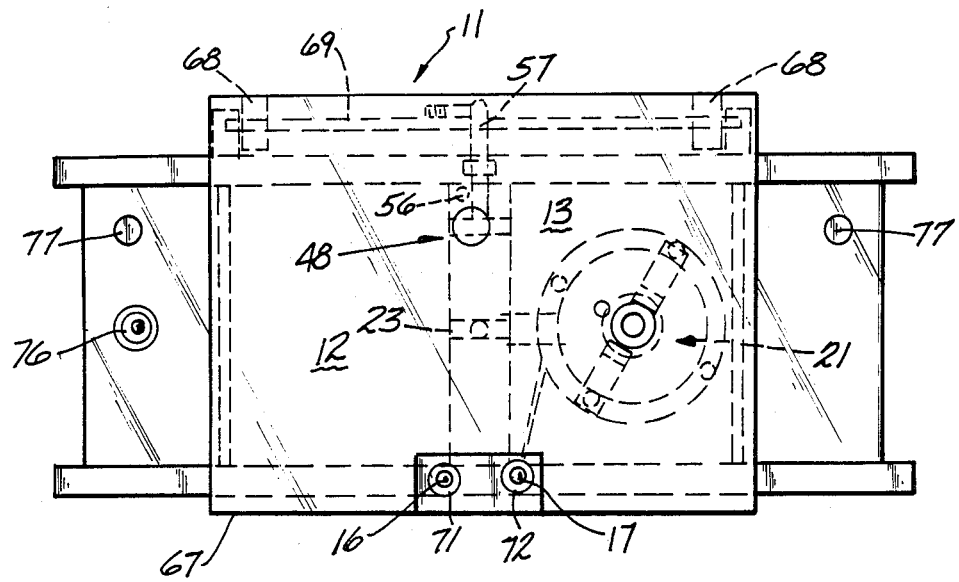
FIG. 2 is a top plan view of the illustration of FIG. 1 assembled.
Figure 3:
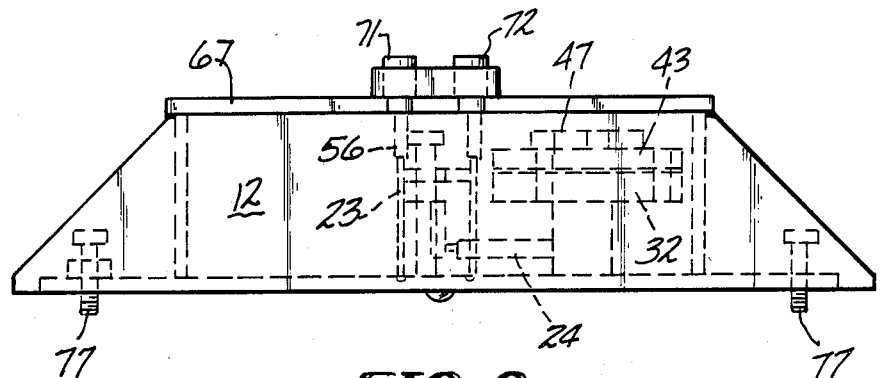
FIG. 3 is a front elevation.
Figure 4:
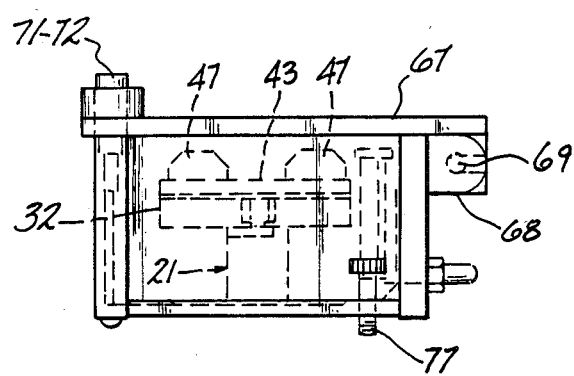
FIG. 4 is an elevational view of the right end of FIG. 2.

The cover 67 removably hinged by a pair of spaced U-shaped members 68—68 engaging rod 69, is provided with openings 71 and 72 to accommodate male electrical connectors 16 and 17 as is most apparent in FIG. 2.

A carpenters level 76 and two oppositely disposed adjusting screws 77 are incorporated into base plate 78 to facilitate leveling the surface of the buffer fluid.

The electroelution receptacle operates in the following fashion:

First of all the receptacle is leveled. Then, with the first valve 21 (in compartment 13) in the open position an appropriate conductive salt of greater than two molar is pipetted into reservoir 28 until overflow occurrs at overflow outlet 23. Obviously the height of the overflow outlet controls the height or level of salt in the reservoir.

Next the valve stem 26 is rotated to the second or closed position.

A gel slice containing nucleic acids or the like is placed upon specimem tray 32.

With the second valve (the spool valve 48) in the first position in which compartments 12 and 13 communicate with one another buffer liquid is introduced until overflow occurs at overflow outlet 56. Overflow at outlet 56 signals the proper level of buffer liquid relative to specimen tray 32.

Tray cover 43 is placed over specimen tray 32.

Next the cover 43 is grasped by buttons 47—47 and the first valve 21 returned to the open position.

Thereafter hinged receptacle lid or cover 67 is attached to hinge rod 69 and the cover dropped to the closed position. During this occurrence the cover 67 contacts the head 66 of spool valve stem 57 move the valve to the second position in which communication between compartments 12 and 13 is cut off.

Power cords are attached and appropriate power levels are applied for appropriate intervals.

Upon completion of the electroelution process power is disconnected; cover 67 removed and the first valve is returned to the second or closed position.

The second valve (spool valve 57) is moved downardly to its third position permitting the buffer fluid to drain to atmosphere through conduit 54 lowering the level of buffer fluid well below the level of the floor of the specimen tray 32.

The recovered concentrated biological is now pipetted out of the reservoir 28 in condition for precipitation and further processing.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An electroelution receptacle useful to remove charged particles such as biological substances from a gel slice comprising at least two major fluid tight compartments separated by a bridge element, a first valve disposed in one compartment including a valve body and a valve stem within said valve body, a conduit connecting said valve body to the other compartment, through said bridge element, said valve stem having a central cavity defining a recovery reservoir, said valve stem being movable from a first position in which said first valve is open so that said recovery reservoir communicates through said conduit with an overflow outlet to a second position in which said first valve is closed and said overflow outlet is cut off, said valve stem supporting at one end a gel specimen tray, a closure member for covering said specimen tray and making a releasable keyed connection with said specimen tray operable manually to move said valve stem to said first and second positions of said valve stem, selectively.

2. The electroelution receptacle of claim 1 in which a gasket means is disposed between the valve stem and the valve body to increase the integrity of the valve when in the closed position.

3. The electroelution receptacle of claim 2 in which the valve stem is formed with a vent having an outlet communicating with said recovery reservoir and a second outlet communicating with said valve body.

4. The electroelution receptacle of claim 3 in which the valve is formed with stop means for limiting the motion of the valve stem relative to the valve body and for indicating the open or closed condition of the valve.

5. The electroelution receptacle of claim 4 in which the specimen tray defines an annular recess offset from said valve stem.

6. The electroelution receptacle of claim 5 in which said one compartment contains an electrode, and the electrode disposed in said one compartment encircles said first valve.

7. The electroelution receptacle of claim 6 in which said conduit communicates with said other compartment and said overflow outlet is positioned at a predetermined elevation so as to control the level of a fluid in said recovery reservoir.

8. The electroelution receptacle of claim 7 in which a second valve is disposed in said bridge element, said first valve being movable from (a) a first or open position in which said compartments communicate with each other, to (b) a second or closed position cutting off communication, to (c) a third position in which both compartments are open to atmosphere.

9. The electroelution receptacle of claim 8 including a hinged receptacle cover having an open and a closed position, said second valve being formed with an operating head making a driving connection with said receptacle cover, said cover being operable to move said second valve from the first position to the second position when said receptacle cover moves from the open position to the closed position.

10. The electroelution receptacle of claim 9 which includes a carpenters level and means for adjusting the level.

11. The electroelution receptacle of claim 10 in which the second valve is fitted with a vent to atmosphere to avoid siphoning action when the second valve is moved selectively to its various positions.

12. The electroelution receptacle of claim 11 in which liquid level in each compartment is controlled when the second valve is in the first position by a normally open overflow conduit leading to the atmosphere.

* * * * *